US00PP24965P2

(12) United States Plant Patent
Van Der Kroft

(10) Patent No.: US PP24,965 P2
(45) Date of Patent: Oct. 14, 2014

(54) ***HIBISCUS* PLANT NAMED 'CARPA'**

(50) Latin Name: *Hibiscus syriacus*
Varietal Denomination: CARPA

(76) Inventor: Paul Van Der Kroft, Strathroy (CA)

( * ) Notice: Subject to any disclaimer, the term of this patent is extended or adjusted under 35 U.S.C. 154(b) by 140 days.

(21) Appl. No.: 13/507,744

(22) Filed: Jul. 24, 2012

Related U.S. Application Data

(60) Provisional application No. 61/574,219, filed on Aug. 1, 2011.

(51) Int. Cl.
*A01H 5/00* (2006.01)

(52) U.S. Cl.
USPC ..... Plt./257

(58) Field of Classification Search
CPC ..... A01H 5/02; A01H 5/00
USPC ..... Plt./257
See application file for complete search history.

(56) References Cited

PUBLICATIONS

Upov Pluto Plant Variety Database 201305, *Hibiscus* Carpa, retrieved on Feb. 26, 2014, retrieved from the Internet at <https://www3.wipo.int/pluto/user/en/index.jsp> one page.*

* cited by examiner

*Primary Examiner* — June Hwu

(57) ABSTRACT

A new cultivar of *Hibiscus* named 'CARPA' that is characterized by upright habit, strongly conspicuous leaf variegation and double flowers of the violet color group that are sterile and open completely. In combination these traits set 'CARPA' apart from all other existing varieties of *Hibiscus* known to the inventor.

2 Drawing Sheets

Genus: *Hibiscus*.
Species: *syriacus*.
Denomination: 'CARPA'.

BACKGROUND OF THE INVENTION

The present invention relates to a new and distinct cultivar of *Hibiscus*, known commonly as Rose of Sharon, and considered an ornamental shrub or small tree for use in garden and landscape. The new cultivar is of the family Malvaceae, known botanically as *Hibiscus syriacus*, and will be referred to hereinafter by the cultivar name 'CARPA'.

'CARPA' was discovered in 2000 as a naturally occurring branch mutation of the parent, an individual *Hibiscus syriacus* 'Ardens' (unpatented). Discovery occurred in a growing crop of 'Ardens' at the inventor's nursery in Strathroy, Ontario, Canada. The inventor selected 'CARPA' based on the criteria of bold leaf variegation, flower traits including color and sterility.

The distinguishing traits of 'CARPA' are strongly conspicuous leaf variegation, with yellow color fading to white as foliage matures, double flowers that open completely, and are sterile. The closest comparison plants are *Hibiscus* 'Meehanii' (unpatented) and *Hibiscus* 'America Irene Scott' (U.S. Plant Pat. No. 20,579). Comparison plant 'Meehanii' produces flower buds that are burgundy in color, and rarely open completely, while the comparison plant 'America Irene Scott' exhibits weak foliage variegation, and produces flowers that are pale bluish-pink in color. 'CARPA' is distinguishable from *Hibiscus* 'Meehanii' by consistent flowering of blossoms that open completely, and is distinguishable from 'American Irene Scott' by strongly conspicuous leaf variegation, flower color, and dramatic color combination of foliage and flower.

'CARPA' exhibits robust upright growth habit, medium branch density, semi-upright branch attitude, brown stems, boldly variegated foliage ranging from mid-green to yellow on young leaves, with the yellow color fading to white as leaves mature. Showy, ruffled, double flowers are of the violet color group, with dark contrasting centers of the red-purple color group. The flower of 'CARPA' is sterile and opens completely. Branching is compact in young plants, opening at maturity. Plants of 'CARPA' are 1.8 meter in height and 1.2 meter in width at maturity.

Suitable cultivation includes full sun, well-draining humus-rich, fertile soil, given regular water during growing periods and then reduced to minimal water. Hardiness is USDA Zone 6. 'CARPA' is recommended for use as a garden specimen, landscape planting, and as a container plant. In the garden 'CARPA' can be espaliered, pruned into a hedge, or easily pruned into a single trunk tree. 'CARPA' is winter deciduous and, depending on placement, can be drought tolerant.

'CARPA' was first asexually propagated in Strathroy, Ontario at the inventor's nursery. The inventor conducted asexual propagation in 2004 using the method of softwood cuttings. Since that time, under careful observation, the distinguishing characteristics of 'CARPA' have been determined fixed, stable, uniform, and have been shown to reproduce true to type in successive generations of asexual propagation.

The inventor filed an application for Canadian Plant Breeders Rights for 'CARPA', application number 09-6661, application date Jun. 9, 2009. The application was granted on Feb. 24, 2012, grant number 4283.

No sales or offers for sale have been made anywhere in the world at the time of filing this plant patent application.

SUMMARY OF THE INVENTION

The following represent the distinguishing characteristics of the new *Hibiscus* cultivar named 'CARPA'. In combination these traits set 'CARPA' apart from all other existing varieties of *Hibiscus* known to the inventor. 'CARPA' has not been tested under all possible conditions and phenotypic differences may be observed with variations in environmental, climatic, and cultural conditions, however, without any variance in genotype.

1. 'CARPA' exhibits robust upright growth habit.
2. 'CARPA' exhibits strongly conspicuous leaf variegation ranging from mid-green and yellow, with the yellow color fading to white as foliage matures.
3. 'CARPA' bears double flowers in the violet color group with dark contrasting centers in the red-purple color group.
4. The flower of 'CARPA' is sterile.
5. The flower of 'CARPA' opens completely.
6. At maturity, plants of 'CARPA' are 1.8 meter in height and 1.2 meter in width.
7. 'CARPA' prefers full sun in well-drained humus-rich, fertile growing media, with regular water during periods of growth.
8. 'CARPA' is suitable for use as a garden specimen, landscape planting, and as a container plant.
9. 'CARPA' is hardy to at least USDA Zone 6.

BRIEF DESCRIPTION OF THE DRAWINGS

The accompanying color drawings illustrate the overall appearance of 'CARPA' showing color of foliage and flower as true as is reasonably possible to obtain in color reproductions of this type.

Drawing labeled

Drawing labeled

Figure 1:
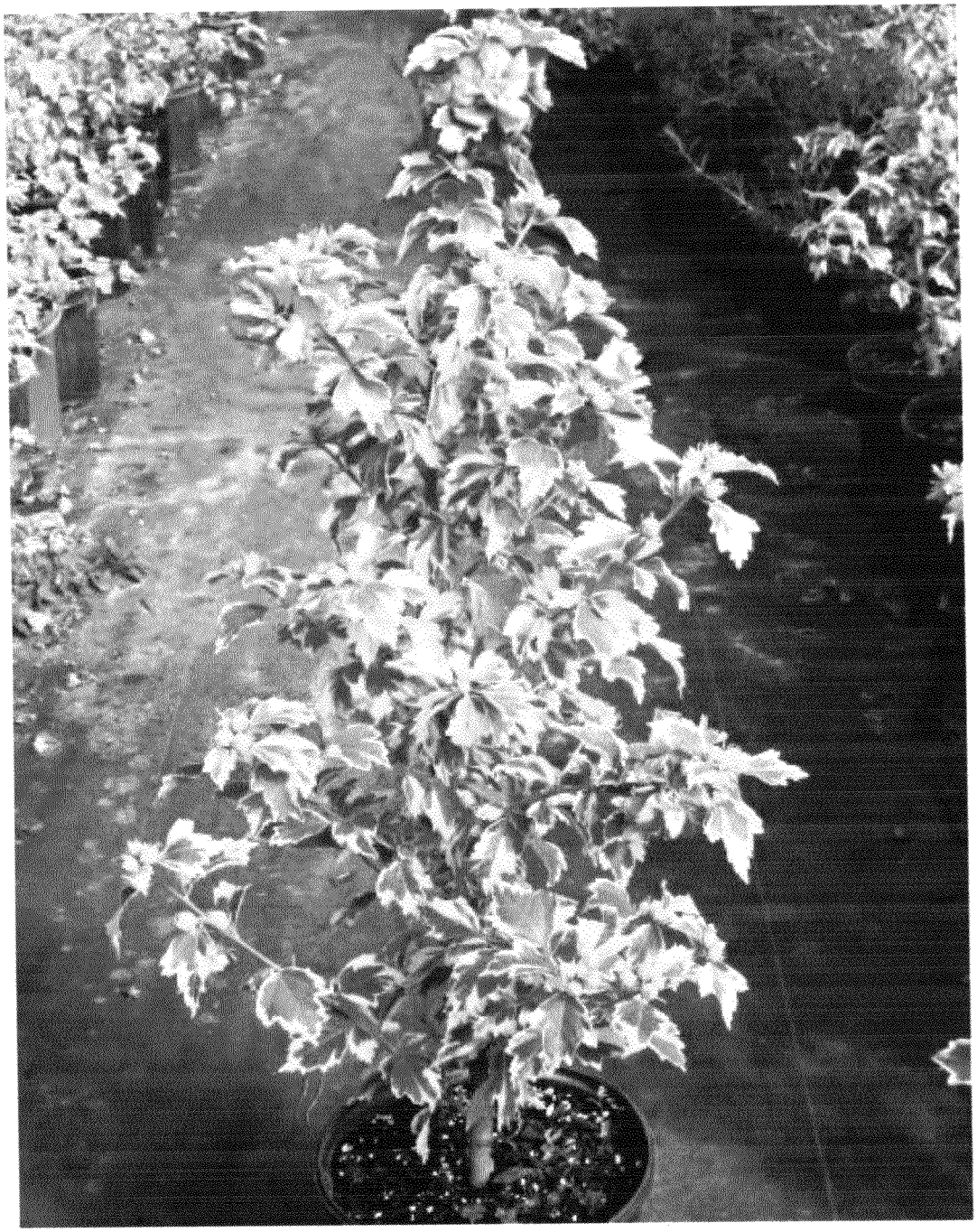
FIG. 1 depicts a 1-liter container plant of 'CARPA', growing out-of-doors.
Figure 2:
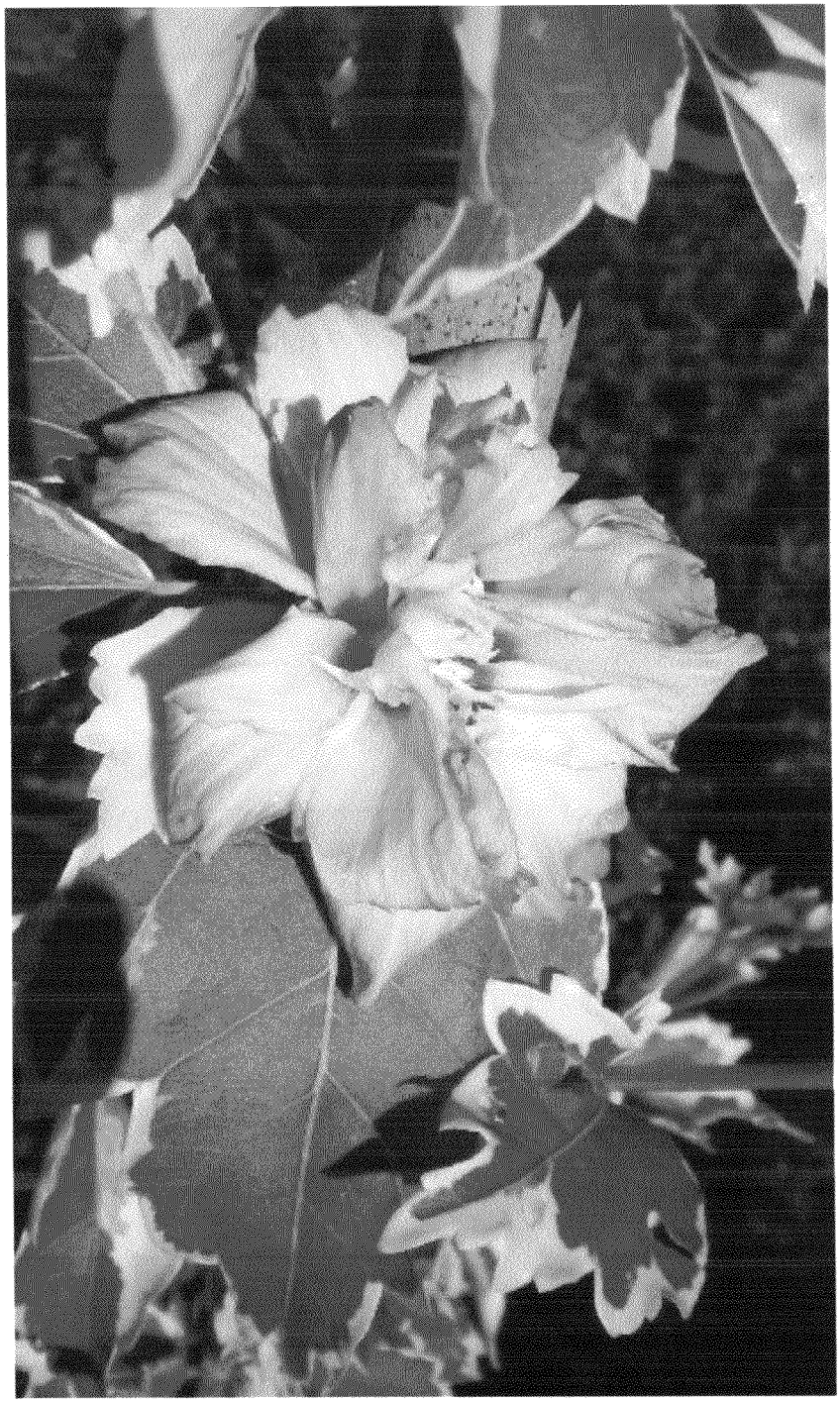
FIG. 2 depicts a close-up view of the flower on a 12-month-old plant of 'CARPA' in Arroyo Grande, Calif., USA.

Drawings were made using conventional techniques and although foliage and flower color may appear different from actual color due to light reflectance, they are as accurate as possible by conventional photography.

BOTANICAL DESCRIPTION OF THE PLANT

The following is a detailed description of the new *Hibiscus* cultivar named 'CARPA'. Data was collected during 2012 in Arroyo Grande, Calif. from 12-month-old plants grown out-of-doors in 2-liter containers. Color determinations are in accordance with the fifth edition (2007) of The Royal Horticultural Society Colour Chart except where general color terms of ordinary dictionary significance are used. The growing requirements are similar to the species.

Botanical classification: *Hibiscus syriacus* 'CARPA'.
Genus: *Hibiscus.*
Species: *syriacus.*
Denomination: 'CARPA'.
Family: Malvaceae.
Common name: Rose of Sharon.
Uses: Ornamental landscape shrub or small tree, container plant and specimen plant.
Parentage: *Hibiscus syriacus* 'CARPA' was discovered by the inventor as a naturally occurring branch mutation of the parent, an individual *Hibiscus* 'Ardens' (unpatented).
Vigor: Vigorous.
Growth habit: Upright.
Plant dimensions in first year: 30 cm in height and 20 cm in width.
Plant dimensions in five years: 1.2 meter in height and 1.8 meter in width.
Hardiness: USDA Zone 6.
Propagation: Soft or hardwood cuttings.
Root system: Fine and fibrous.
Cultural requirements: Full sun and humus-rich, fertile, well-draining soil, giving regular water during periods of growth.
Pest susceptibility: Susceptible to aphids and whitefly.
Disease susceptibility: None known to the inventor.
Type: Perennial.
Time to initiate rooting (average): 14-28 days in a greenhouse with bottom heat to produce roots on semi-ripe cuttings.
Crop time: Requires 36 months to produce a five-gallon container plant from a rooted cutting.
Seasonal interest: Variegated foliage leafs out late spring, and flowers bloom mid-summer.
Special considerations: Prefers heat, tolerates some drought. Protect roots of young plants with mulch and prune plants to shape.

Stem:
- *Branching habit.*—Compact when young and opening in maturity.
- *Lateral branch quantity* (*range*).—7-14 in number per 1-litre container plant.
- *Stem length.*—10 cm in length.
- *Stem diameter.*—0.30 cm in diameter.
- *Stem color.*—New stem growth 133A becoming darker when mature, eventually N199B.
- *Stem texture.*—Smooth, glabrous.
- *Stem strength.*—Strong.
- *Stem surface.*—Glabrous.
- *Internode length* (*average*).—1.50 cm.
- *Stem shape.*—Cylindrical.
- *Trunk dimensions.*—12 cm in height and 1 cm in diameter.
- *Trunk shape.*—Cylindrical.
- *Trunk surface.*—Scurfy.
- *Trunk color.*—N199B.

Foliage:
- *Type.*—Deciduous.
- *Leaf arrangement.*—Spirally arranged.
- *Leaf quantity* (*average*).—6 per lateral stem; 70 per 1-litre container plant.
- *Leaf length* (*average*).—3-5 cm in length.
- *Leaf width* (*average*).—1.50-4.50 cm in width.
- *Leaf color* (*both surfaces*).—N138A, except margin.
- *Margin color* (*both surfaces*).—10D in spring and early summer, fading to 157D in full summer sun.
- *Leaf division.*—Simple.
- *Leaf shape.*—Three-lobed.
- *Leaf margin.*—Coarsely toothed.
- *Leaf base.*—Rounded.
- *Leaf apex.*—Acute.
- *Leaf venation.*—Pinnate.
- *Vein color* (*adaxial surface*).—139D.
- *Vein color* (*abaxial surface*).—139D.
- *Leaf surface* (*adaxial*).—Glabrescent.
- *Leaf surface* (*abaxial*).—Glabrescent.
- *Leaf attachment.*—Petiolate.
- *Petiole dimensions.*—0.75 cm in length and 1 mm in width.
- *Petiole color.*—139C.
- *Petiole surface.*—Flocculent.
- *Stipules.*—Present.

*Stipule shape*.—Lanceolate.
*Stipule color*.—139C.
*Stipule dimensions*.—3 mm in diameter and 0.25 cm in length.
*Foliar fragrance*.—None observed to date.

Inflorescence:
*Inflorescence type*.—Double flower.
*Flower shape*.—Rotate.
*Flower form*.—Showy and ruffled.
*Flower sexuality*.—Sterile.
*Flower quantity* (*average*).—1 flower and 6 buds per 1-litre container plant.
*Flower dimensions*.—3.50 cm in depth and 6 cm in diameter.
*Aspect*.—Facing outward.
*Petals* (*range*).—16-18 in number per inflorescence.
*Petal basal color*.—60A.
*Adaxial petal color* (*range*).—84A fading to 84D.
*Abaxial petal color* (*range*).—84A fading to 84D.
*Petal length* (*average*).—3 cm in length.
*Petal width* (*average*).—2.75 cm in width.
*Petal margin*.—Medium serration and undulation.
*Petal shape* (*range*).—Orbicular to obovate.
*Petal arrangement*.—Petals overlapping.
*Unfused or fused*.—Petals are unfused in relationship to one another but individually adnate to the stamen column.
*Petal surface* (*abaxial and adaxial surfaces*).—Glabrescent.
*Bud color* (*combination*).—154D and 144A.
*Bud apex* (*range*).—Truncate to obtuse.
*Bud base*.—Rounded.
*Bud shape*.—Urceolate.
*Bud dimensions*.—1 cm in height and 0.75 cm in diameter.
*Bud surface*.—Pubescent.
*Epicalyx*.—7-lobed. Lobes lanceolate, fused at base.
*Lobe dimensions*.—15-18 mm in length, 2-3 mm in width.
*Lobe color* (*variegated*).—154D and 144A.
*Lobe surface*.—Lanate.
*Calyx shape*.—Campanulate.
*Calyx color* (*variegated*).—154D and 144A.
*Calyx dimensions*.—1.75 cm in height and 2 cm in diameter.
*Calyx surface* (*abaxial and adaxial*).—Lanate.
*Sepals*.—7 in number.
*Sepals fused or unfused*.—Basally fused.
*Sepal color* (*variegated*).—154D and 144A.
*Sepal apex*.—Apiculate.
*Sepal base*.—Truncate.
*Sepal shape*.—Lanceolate.
*Sepal margin*.—Entire.
*Dimensions of sepal*.—1.50 cm in height and 1 cm in width.
*Peduncle dimensions*.—4 cm in length and 2-3 mm in width.
*Color of peduncle*.—144B.
*Surface of peduncle*.—Setose.
*Natural flowering season*.—July and August.
*Persistent or self-cleaning*.—Self-cleaning.
*Lastingness of flower*.—1-2 days on the plant.
*Fragrance*.—None observed to date.

Reproductive organs:
*Stamens*.—40-50 in number, fused at base and clasping the style.
*Stamen length*.—5-7 mm.
*Color of stamens*.—160D.
*Pistil*.—1 in number.
*Pistil length*.—9 mm.
*Pistil color*.—160D.
*Stigma arrangement*.—Exserted.
*Stigma form*.—Filament.
*Stigma length*.—9 mm.
*Stigma color*.—160D.
*Ovary position*.—Superior.
*Ovary shape*.—Globular.
*Ovary surface*.—Pubescent.
*Ovary color*.—154C.
*Ovary dimensions*.—0.75 cm in height and 0.50 cm in diameter.
*Seeds*.—None found in repeated observations.

The invention claimed is:

1. A new and distinct variety of *Hibiscus* plant named 'CARPA' as described and illustrated herein.

* * * * *